United States Patent [19]

Rosenberger et al.

[11] 4,439,615
[45] Mar. 27, 1984

[54] MERCAPTOPHENOL STABILIZERS

[75] Inventors: Siegfried Rosenberger; Samuel Evans, both of Riehen, Switzerland; Bernard Gilg, St. Louis, France

[73] Assignee: Ciba-Geigy Corporation, Ardsley, N.Y.

[21] Appl. No.: 399,502

[22] Filed: Jul. 19, 1982

Related U.S. Application Data

[63] Continuation-in-part of Ser. No. 239,712, Mar. 2, 1981, abandoned.

[30] Foreign Application Priority Data

Mar. 3, 1980 [CH] Switzerland .................. 1665/80

[51] Int. Cl.³ .................................. C07C 149/40
[52] U.S. Cl. .................................. 560/15; 560/147; 568/51; 568/62; 524/289; 524/284; 524/369; 524/419
[58] Field of Search .............. 560/15, 147; 568/51, 568/62

[56] References Cited

U.S. PATENT DOCUMENTS 3,504,012 3/1970 Braus et al. .................. 560/15
4,020,042 4/1977 Cottman .................. 560/147 X
4,284,790 8/1981 Hinsken et al. .................. 560/15

*Primary Examiner*—Bernard Helfin
*Attorney, Agent, or Firm*—Harry Falber

[57] ABSTRACT

Compounds of the formula V

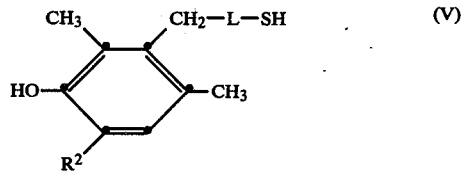

wherein $R^2$ is straight-chain or branched alkyl of 1 to 8 carbon atoms, cycloalkyl, aryl, alkaryl or aralkyl, L is a bivalent radical, for example $-SCH_2CO.O(CH_2CH_2S)_y-CH_2CH_2-$ or $-O.COC_pH_{2p}-$ wherein y is a number from 1 to 3 and p is a number from 1 to 18.

5 Claims, No Drawings

MERCAPTOPHENOL STABILIZERS

This is a continuation-in-part application of application Ser. No. 239,712, filed Mar. 2, 1981, now abandoned.

The present invention relates to novel mercaptophenols which are useful stabilisers for organic material.

It is already known to stabilise organic material, especially polymers, with mercaptophenol stabilisers which develop their action when, for example, they are incorporated in the material to be stabilised. When stabilising polymers, especially against oxidation, it can be very advantageous to graft the respective stabiliser, in the presence of a radical initiator, onto the polymer. The grafting of stabilisers onto polymers is described in detail in German Offenlegungsschrift No. 2 509 654. Other relevant publications incorporated herein by reference are an item in Chemical Age 17/24, August 1979, page 5, and an article in British Plastic and Rubber, April 1977, pp. 25-26. In this latter publication, reference is made on page 26 to further publications by Gerald Scott in various journals. In addition, attention is also drawn to a Japanese publication "Network bound antioxidants in diene rubber" in Nippon Gomu Kyokaishi 1977, 50(8), 548-552, (Chem. A. 87, (1977) 44 (168997a).

The bonding of stabilisers to polymers through sulfur bridges has the following advantages:

(a) the stabilisers are lost neither by evaporation nor by extraction, (b) low or no migration has toxicological advantages.

Compared with the known similar compounds, the mercaptophenols of this invention are more effective after they have been grafted onto preformed polymers.

Accordingly, the invention provides compounds of the formula I

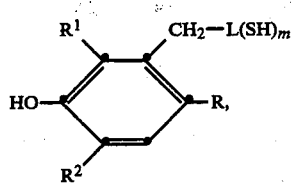
(I)

wherein m is 1 or 2, $R^1$ and $R^2$ are the same or different and are straight-chain or branched alkyl of 1 to 18 carbon atoms, cycloalkyl, aryl, alkaryl or aralkyl, whilst $R^2$, in contrast to $R^1$, can also be hydrogen, R is alkyl of 1 to 12 carbon atoms or hydrogen, and if m is 2, L is one of the trivalent radicals

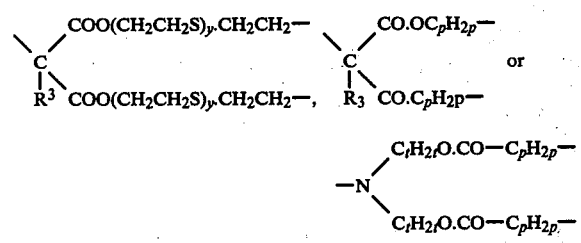

or if m is 1, is one of the bivalent radicals $—SCH_2CO.OCH_2CH_2—$ $—SCH_2CO.O(CH_2CH_2S)_yCH_2CH_2—$, $—O.CO.C_pH_{2p}—$, $—SCH_2CH_2O.CO.C_pH_{2p}—$, $—OC_tH_{2t}NH.CO.C_pH_{2p}—$, $—NH—C_tH_{2t}NH.CO.C_pH_{2p}—$, $—S.C_pH_{2p}—$, $—NH.CO.C_pH_{2p}—$, $—N$ $H—C_pH_{2p}—$, $—O.C_pH_{2p}—$, $—OC_tH_{2t}OCO.C_pH_{2p}—$, $—NH.C_tH_{2t}O.CO.C_pH_{2p}—$ in which formulae $R^3$ is alkyl of 1 to 18 carbon atoms, hydrogen, or the radical

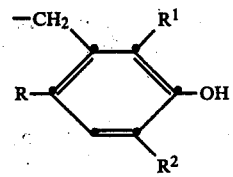

and y is a number from 1 to 3 and t is a number from 1 to 18, and compounds of the formula II

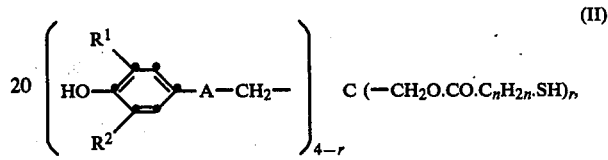
(II)

wherein $R^1$ and $R^2$ are as defined for formula I, r is 1, 2 or 3, and A is the radical

wherein c and n are the same or different and are a number from 1 to 12, and compounds of the formula III

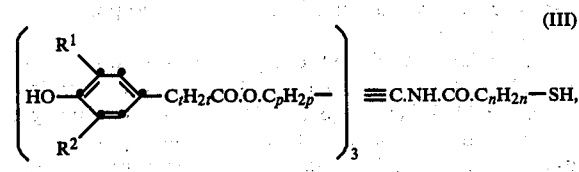
(III)

wherein $R^1$ and $R^2$ are as defined for formula I, t and p are the same or different and are a number from 1 to 18, and n is a number from 1 to 12, and compounds of the formula IV

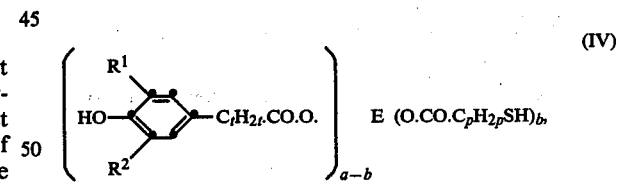
(IV)

wherein $R^1$ and $R^2$ are as defined for formula I, t and p are the same or different and are a number from 1 to 18, a is 4 and b is 1, 2 or 3, or a is 2 and b is 1, or a is 3 and b is 1, and E is a divalent to quadrivalent hydrocarbon radical which is derived from a $C_2$-$C_{12}$alkylenepolyol, glycerol or pentaerythritol.

$R^1$ and $R^2$ as alkyl radicals can be e.g.: methyl, isopropyl, n-butyl, sec-butyl, tert-butyl, tert-amyl, 2-ethylhexyl, n-octyl or 1,1,3,3-tetramethylbutyl. α-Branched alkyl radicals of 3 to 8 carbon atoms are preferred.

$R^1$ and $R^2$ as cycloalkyl can be e.g.: cyclopentyl, cyclohexyl, cycloheptyl or cyclooctyl. Cyclopentyl and cyclohexyl are preferred.

$R^1$ and $R^2$ as aralkyl can be benzyl, α-phenylethyl and 2-phenyl-isopropyl. The preferred identities are α-phenylethyl and 2-phenyl-isopropyl.

$R^1$ and $R^2$ as alkaryl can be e.g. tolyl, xylyl, 2,6-diethyphenyl or 4-tert-butylphenyl.

$R^1$ and $R^2$ as aryl are e.g. phenyl, α-naphthyl or β-naphthyl, with phenyl being the preferred identity.

$R^3$ can have the same meanings as $R^1$ and $R^2$ if the latter are alkyl of 1 to 18 carbon atoms.

It is preferred that $R^2$ is tert.-butyl.

Preferred compounds of formula I correspond to the compounds of formula V

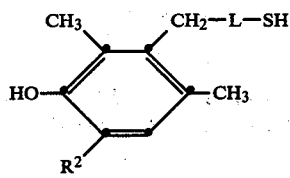
(V)

wherein $R^2$ is straight-chain or branched alkyl of 1 to 8 carbon atoms, $C_5$–$C_8$ cycloalkyl, $C_6$–$C_{10}$-aryl, $C_7$–$C_{10}$-alkaryl or $C_7$–$C_{10}$-aralkyl, L is one of the bivalent radicals —$SCH_2CO.OCH_2CH_2$—, —$SCH_2CO.O(CH_2CH_2S)_y$—$CH_2CH_2$—, —$O.CO.C_pH_{2p}$—, —$SC_pH_{2p}$— or —$O.C_pH_{2p}$—, y is a number from 1 to 3 and p is a number from 1 to 18.

Particularly preferred compounds are those compounds of formula V wherein L is a bivalent radical —$SCH_2CO.O(CH_2CH_2S)_y$—$CH_2CH_2$— with y being a number from 1 to 3, or —$O.CO.C_pH_{2p}$— with p being a number from 1 to 18, especially the compounds of formulae

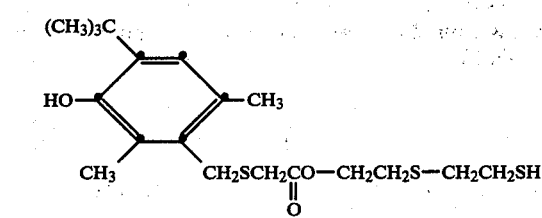

and

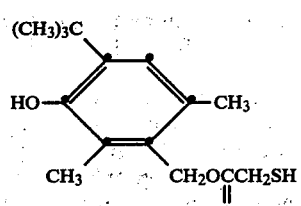

A preferred compound of the formula II has the following structure:

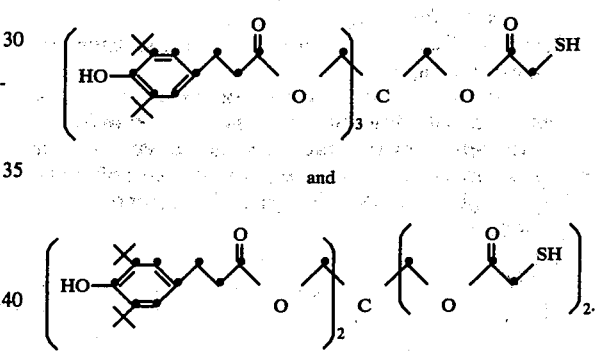

wherein $R^2$ is —$CH_3$ or tert-butyl.

Particularly preferred compounds of the formula IV are those of the following structure

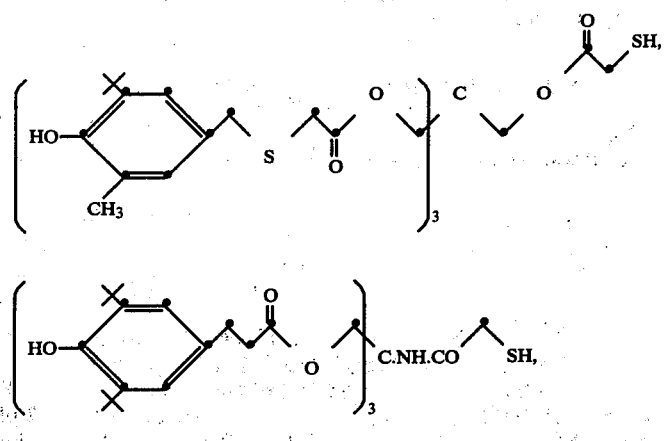

Examples of the compounds of the invention are:

according to formula II according to formula III according to formula IV 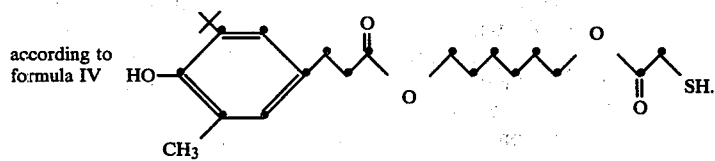

The compounds of this invention are obtained by methods which are known per se. The compounds of the formula I are obtained e.g. in accordance with the following reaction schemes:

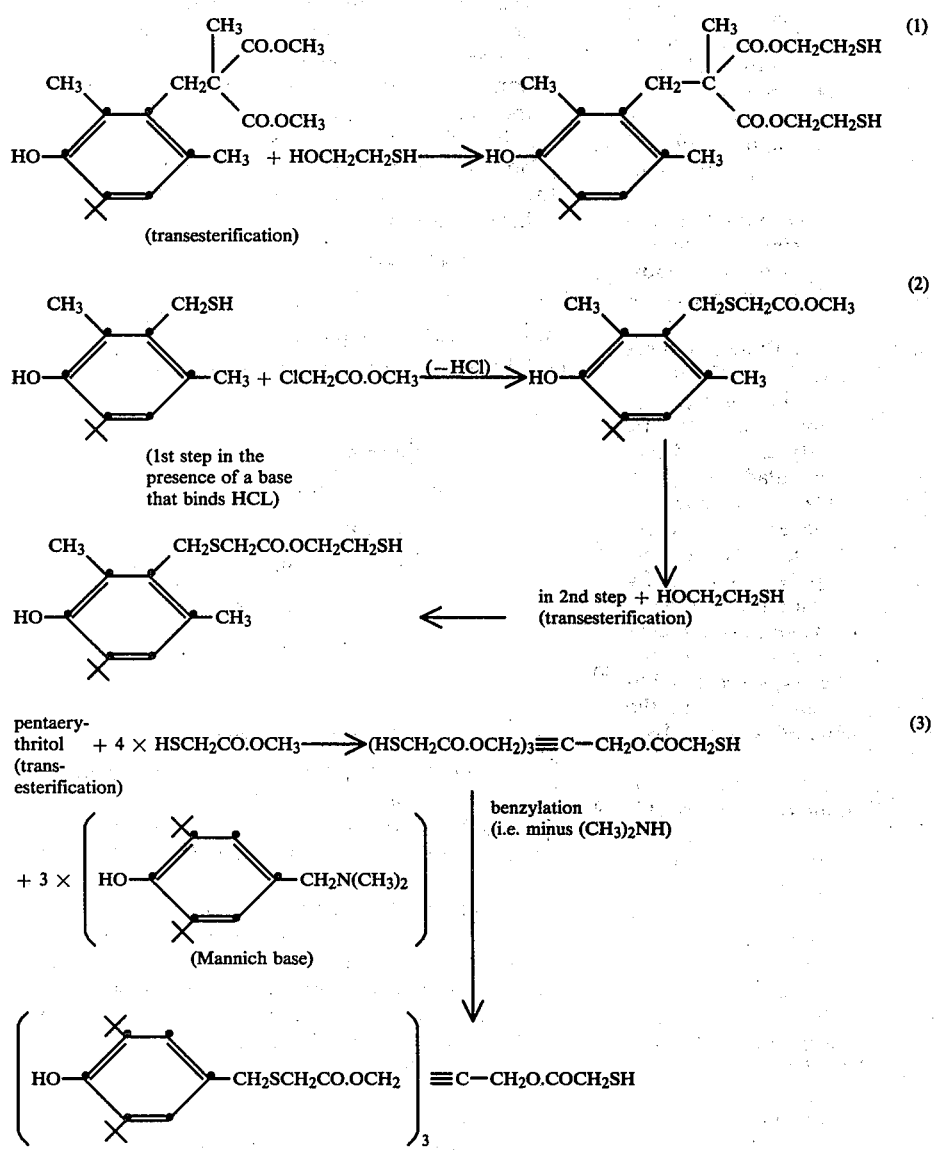

The compounds of the formulae II, III and IV are obtained by analogous procedures.

The starting materials employed for obtaining the compounds of the invention are known compounds which are likewise prepared by methods that are known to the skilled person.

The invention also relates to the use of the compounds of the compounds of the formulae I to IV and of a known compound, as stabilisers for organic material, in particular for obtaining stabilised polymers by grafting these compounds onto the polymers.

The compounds employed as stabilisers are, in addition to the compounds of the formula I and, in particular, the preferred embodiments of the compounds of the invention which have been specified hereinabove, also the known compound of the formula

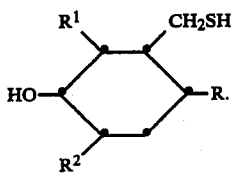

(X)

Methods of obtaining this known compound are also known, so that it is unnecessary to enter into any further discussion of the matter.

The mercaptophenols of this invention are grafted onto the preformed polymers by reacting the polymers with the mercaptophenols in the presence of a radical initiator. The reaction can be carried out in aqueous emulsion or suspension, in solution, or in the melt. It is advantageous to carry out the reaction under those conditions which are similar to those employed for obtaining the polymer. In this connection, the preferred procedure is to carry out the grafting in aqueous emulsion.

Suitable radical initiators are organic peroxides, hydroperoxides or persulfates and combinations thereof with amines or $Fe^{2+}$ salts, preferably azo compounds. The weight ratio of stabiliser to radical initiator is not critical and is 100:1 to 0.25:1.

The stabilisers can be reacted with all those polymers listed in German Offenlegungsschrift No. 2 509 654, i.e. with polyolefins, polystyrene, polyvinyl chloride, polyamides, polyesters, natural or synthetic rubbers, ethylene/propylene rubber, styrene/butadiene, acrylonitrile/butadiene/styrene, polybutadiene, polyisoprene, copolymers of methacrylate/butadiene/styrene and methylmethacrylate/butadiene/styrene, especially in the form of latices. It is, of course, also possible to use mixtures of polymers. The polymers normally have a high molecular weight, e.g. such that the polymer is film- or filament-forming. However, low molecular polymers, e.g. polymers which are still liquid, can also be used if the adducts are to be employed as additives for other polymers. Suitable latices are also the following polymers: NR, BR, NBR, SCR, CR, MBS, ABS.

In the practice of this invention, the antioxidant is added to the polymer in an amount of 0.001 to 5%, preferably 0.1 to 1%, based on the weight of the polymer, if it is desired to modify the properties of the polymer. If, on the other hand, the antioxidant is added in order to prepare an adduct that can be used to modify the properties of another polymer, then larger amounts can be used. In the present reaction, where the antioxidant is a thiol, it is possible to use such large amounts as 300 to 500% by weight, preferably 50% by weight. The reaction temperature is in the range from 0° to 200° C., with the preferred range being from 50° to 130° C., but for latex systems it is from 40° to 60° C. In a second step, these graft polymers with a high content of antioxidant are diluted with the starting polymer or with another polymer. This dilution can be effected by mixing latices or solutions or also by blending in the graft copolymer having a high content of antioxidant.

The following polymers can be stabilised utilising the compounds of the invention by means of the described grafting process: polypropylene, polyethylene, polyisoprene, also in the form of natural rubber, polybutadiene, terpolymers of ethylene, propylene and a diene, ethylene/propylene rubber, styrene/butadiene, styrene/butadiene/styrene block copolymers, styrene/butadiene graft copolymers, acrylonitrile/butadiene/styrene graft copolymers, polychloroprene, acrylonitrile/butadiene copolymers, methacrylate/butadiene/styrene graft polymers. (The preferred polymers are underlined).

The starting polymers used for the grafting process can contain further additives, e.g.: further alkylated phenols as antioxidants, light stabilisers such as 2-(2'-hydroxyphenyl)benztriazoles, 2-hydroxybenzophenones, nickel compounds, sterically hindered amines, phosphites, thioethers, fillers, plasticisers, lubricants, flame retardants, antistatic agents.

Accordingly, the invention also relates to:
(a) the indicated utility, which comprises grafting the compounds of the formulae I to IV and X, in the presence of a radical initiator, onto a polymer,
(b) organic polymers stabilised by compounds of the formulae I to IV or X,
(c) the polymers so stabilised, which contain compounds of the formulae I to IV or X as stabilisers,
(d) stabilised polymers onto which the stabilisers have been grafted.

PREPARATORY EXAMPLES

EXAMPLE 1

5-mercapto-3-thia-n-pentyl S-(3,5-dimethyl-4-tert-butyl-3-hydroxybenzyl)thioglycolate

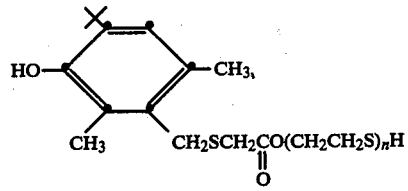

n = 2

A. Methyl ester precursor 22.7 g of 2-tert-butyl-4,6-dimethyl-5-chloromethylphenol[1] are dissolved in 100 ml of dimethyl acetamide, and this solution is added dropwise, with stirring, to a mixture of 50 ml of dimethyl acetamide, 14 ml of triethylamine and 12 g of methyl thioglycolate. In the course of this addition, the temperature rises to about 35° C. The batch is then stirred for 6 hours at 75° C. Chromatographic analysis confirms that virtually no more educt can be detected and that homogeneous methyl S-(3,5-di-tert-butyl-4-tert-butyl-3-hydroxybenzyl)thioglycolate has formed (definition by elemental analysis). The solvent is distilled off in vacuo and triethylamine hydrochloride is removed by treating the above product with water.

[1] Prepared in accordance with the procedure described in "Makromolek.Chemie", Vol, 9, pp. 21–22 (1952).

B. Transesterification with mercaptoethanol to give the final product

With stirring, 29.6 g of methyl ester precursor A, 23.4 g of 2-mercaptoethanol and 0.5 ml of tetrabutyl orthotitanate are heated for 14 hours, under nitrogen, to 140° C. Excess 2-mercaptoethanol is then distilled off in a high vacuum. Methoxy group determination shows that the viscous residue still contains only a small amount of methyl ester, and NMR spectroscopy confirms that it consists of a mixture of mercapto esters of the above structure, in which n=4. The compound of this Example, in which n=2, is separated from mixture in the form of a viscous oil by chromatography and is defined by elemental analysis and SH titration.

EXAMPLE 2

3-hydroxy-4-tert-butyl-2,6-dimethylbenzylthioglycolate

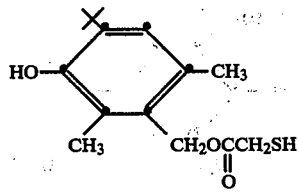

With stirring, 22.6 g of 2-tert-butyl-4,6-dimethyl-4-chloromethylphenol[(1)] and 11.4 g of sodium thioglycolate are reacted, under nitrogen, in 200 ml of dimethyl acetamide for 8 hours at 65° C. Thin-layer chromatography subsequently confirms that virtually no more educt is detectable. The solvent is removed in vacuo and the crude product is taken up in toluene and freed from NaCl by washing with water. After purification by column chromatography, the product is obtained in the form of a viscous resin and is defined by SH content and elemental analysis.
(1) Prepared in accordance with the procedure described in "Makromolek. Chemie", Vol. 9, pp. 21–22 (1952).

USE EXAMPLES

EXAMPLE I 100 g of polybutadiene latex (30% solids content) are stirred at 55° C. under nitrogen. At this temperature the following substances are added:
  (a) 1 g of sodium stearate in 100 ml of $H_2O$,
  (b) 0.3 g of a compound A of the formula

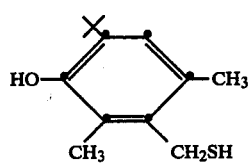

(A)

(c) 0.01 g of azo-bis-isobutyronitrile.

The mixture is stirred for 10 hours, then the resultant emulsion is coagulated by addition of 100 ml of 2.5% sulfuric acid at 55° C. and the precipitated rubber is thoroughly washed with water. After filtration the precipitate is predried for 3 hours at 40° C. in vacuo. The water is removed by passing the rubber 3 times through a cold roller. The rubber is then dried for 12 hours in vacuo at room temperature. The dried rubber is pressed in a hot press at 60° C. to 2 mm sheets (time taken: 20 minutes). The effectiveness of the additive is tested by subjecting the rubber samples to heat ageing. This is accomplished by immersing the samples in silicone oil at 160° C. for 20 minutes. The gel content at the end of the heat ageing serves as index of the ageing and is determined as follows: 1 g of polybutadiene is dissolved overnight at room temperature in 100 ml of toluene. The solution is filtered through glass wool and the filtered solution is evaporated to dryness. The gel content is calculated from the equation:

$$\text{gel} = \frac{WS - WR}{WS} \times 100\%$$

in which
  WS = weighed sample (usually 1 g)
  WR = weight of evaporation residue In this experiment, the test results of the heat ageing show that gel development is effectively suppressed by the additive A. In a second experiment the good action of the stabiliser is also demonstrated by ageing.

The ageing in silicone oil is performed however in this case after the specimen has been deposited for 24 hours in ethanol at room temperature.

EXAMPLE II

The procedure of Example I is repeated, except that the compound B

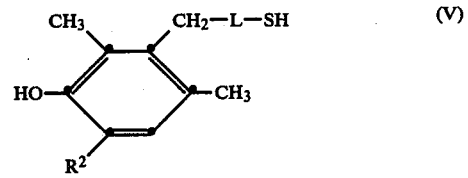

(B)

is substituted for compound A.

In this experiment too the heat ageing (determination of gel formation as in Example I) shows that stabiliser B is also very effective in the polymer.

The test results obtained in Example I are reported in Tables 1 and 2. The results show that the stabiliser system is stable to extraction.

TABLE 1

| Ageing without prior extraction with ethanol | |
|---|---|
| | gel content (%) |
| without stabiliser | 30 |
| stabiliser A | 5 |
| stabiliser B | 6 |

TABLE 2

| Ageing after prior extraction with ethanol | |
|---|---|
| | gel content (%) |
| without stabiliser | 50 |
| stabiliser A | 11 |
| stabiliser B | 5 |

What we claim is:
1. A compound of the formula V

![Formula V structure: benzene ring with CH3, HO, R2, CH3, and CH2-L-SH substituents]

(V)

wherein $R^2$ is straight-chain or branched alkyl of 1 to 8 carbon atoms, $C_5-C_8$-cycloalkyl, $C_6-C_{10}$-aryl, $C_7-C_{10}$-alkaryl or $C_7-C_{10}$-aralkyl, L is one of the bivalent radicals —$SCH_2CO.OCH_2CH_2$—, —$SCH_2CO.O(CH_2CH_2S)_y$—$CH_2CH_2$—, —$O.CO.C_pH_{2p}$—, —$SC_pH_{2p}$— or —O.$C_pH_{2p}$—, y is a number from 1 to 3 and p is a number from 1 to 18.

2. A compound according to claim 1 of the formula V, wherein L is a bivalent radical —SCH$_2$CO.O(CH$_2$CH$_2$S)$_y$—CH$_2$CH$_2$—, wherein y is a number from 1 to 3.

3. A compound according to claim 1 of the formula V, wherein L is a bivalent radical —O.CO.$C_pH_{2p}$—, wherein p is a number from 1 to 18.

4. A compound according to claim 1 of the formula

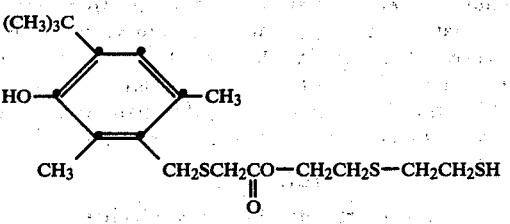

5. A compound according to claim 1 of the formula

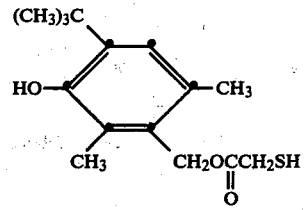

* * * * *